(12) United States Patent
Cabezas Alamos

(10) Patent No.: US 10,412,904 B2
(45) Date of Patent: Sep. 17, 2019

(54) WATERPROOF AND UV (ULTRAVIOLET) RADIATION BLOCKING PROTECTIVE COVER

(71) Applicant: United Plastic Corporation, Quilicura (CL)

(72) Inventor: Patricio Javier Cabezas Alamos, Quilicura (CL)

(73) Assignee: United Plastic, Santiago (CL)

( * ) Notice: Subject to any disclaimer, the term of this patent is extended or adjusted under 35 U.S.C. 154(b) by 292 days.

(21) Appl. No.: 15/409,389

(22) Filed: Jan. 18, 2017

(65) Prior Publication Data

US 2017/0295729 A1 Oct. 19, 2017

(30) Foreign Application Priority Data

Apr. 13, 2016 (CL) .................................. 201600875

(51) Int. Cl.
| | | |
|---|---|---|
| *A01G 13/02* | (2006.01) | |
| *A01G 22/00* | (2018.01) | |
| *A01G 13/06* | (2006.01) | |
| *A01G 13/10* | (2006.01) | |
| *A01N 25/10* | (2006.01) | |

(52) U.S. Cl.
CPC ......... *A01G 13/0237* (2013.01); *A01G 13/06* (2013.01); *A01G 13/105* (2013.01); *A01G 22/00* (2018.02); *A01N 25/10* (2013.01)

(58) Field of Classification Search
CPC ............ A01G 13/0212; A01G 13/0237; A01G 13/0275; A01G 13/0281; A01G 13/043

USPC ................................. 47/20.1, 23.1, 24.1, 29.4
See application file for complete search history.

(56) References Cited

U.S. PATENT DOCUMENTS

| 4,071,975 | A | * | 2/1978 | Tanaka | A01G 13/0275 47/9 |
|---|---|---|---|---|---|
| 5,548,923 | A | * | 8/1996 | Myer | A01G 13/0281 47/32 |
| 5,564,223 | A | * | 10/1996 | Takita | A01G 13/0237 383/120 |
| 5,605,009 | A | * | 2/1997 | Elder | A01G 13/0281 47/32 |
| 6,061,954 | A | * | 5/2000 | Vanier | A01G 13/0237 47/24.1 |
| 6,640,490 | B1 | * | 11/2003 | Boehringer | A01G 13/0281 47/32 |
| 9,565,809 | B2 | * | 2/2017 | Zhang | A61L 11/00 |

(Continued)

FOREIGN PATENT DOCUMENTS

| CN | 201222908 Y | * | 4/2009 | ............. A01G 13/02 |
|---|---|---|---|---|
| CN | 201399435 Y | * | 2/2010 | ............ B07B 13/075 |

(Continued)

*Primary Examiner* — Peter M Poon
*Assistant Examiner* — Danielle A Clerkley
(74) *Attorney, Agent, or Firm* — John Dodds; Adrian Zapatero

(57) ABSTRACT

Waterproof and UV (ultraviolet) radiation blocking protective cover (1) for hanging fruit, CHARACTERIZED by a sheet (10) made of an expanded polyethylene material that blocks ultraviolet radiation (EPE-UV), whose shape is a flat geometric figure, with a main straight cut (11) running from the midpoint to the edge of the sheet and an arrangement of cuts and grooves that make up the attachment system when the cover is fitted on the fruit.

13 Claims, 4 Drawing Sheets

(56) References Cited

U.S. PATENT DOCUMENTS

| | | | | |
|---|---|---|---|---|
| 2001/0051240 A1* | 12/2001 | Denis | .................. | A01G 13/0225 |
| | | | | 428/36.1 |
| 2002/0083641 A1* | 7/2002 | Leppard | ............... | C07D 251/24 |
| | | | | 47/29.4 |
| 2009/0133323 A1* | 5/2009 | Farmer | .................. | A01G 17/04 |
| | | | | 47/9 |
| 2011/0265378 A1* | 11/2011 | Callaway | ............... | A01G 9/243 |
| | | | | 47/1.01 R |
| 2014/0083001 A1* | 3/2014 | Alcov | ................... | A01M 29/24 |
| | | | | 47/20.1 |
| 2016/0309663 A1* | 10/2016 | Cheret | .................... | B32B 27/08 |

FOREIGN PATENT DOCUMENTS

| | | | | | |
|---|---|---|---|---|---|
| CN | 101990835 A | * | 3/2011 | ............. | A01G 13/02 |
| ES | 193383 U | * | 10/1974 | ............. | A01G 13/02 |
| GB | 116947 A | * | 7/1918 | ......... | A01G 13/0281 |
| GB | 707712 A | * | 4/1954 | ......... | A01G 13/0237 |
| JP | H1052180 A | * | 2/1998 | ............. | A01G 13/02 |
| JP | H10165010 A | * | 6/1998 | ............. | A01G 13/02 |

* cited by examiner

WATERPROOF AND UV (ULTRAVIOLET) RADIATION BLOCKING PROTECTIVE COVER

CROSS-REFERENCE TO RELATED APPLICATIONS

This utility patent application claims priority of a Chilean Patent Application Serial Nr. 201600875 filed on Apr. 16, 2016 before the Chilean Patent Office which is incorporated in its entirety as a reference.

BACKGROUND OF THE INVENTION

This invention refers to a protective covering for developing hanging fruit, which protects the fruit from different environmental and climatic conditions, such as rain, frost, fungus growth, excess UV radiation and damage caused by birds, the cover being waterproof and a UV (ultraviolet) radiation blocker that is placed individually on each fruit or cluster of fruit and is easy to install and reusable.

DESCRIPTION OF THE PRIOR ART

The fruit cultivation process often faces a range of environmental and climatic conditions that, if not properly addressed, can severely affect the crop resulting in production losses and, in some cases, lead to total crop failure.

Crops frequently face climatic conditions, which in the past were regular and predictable, meaning that production could adapt or organize itself adequately to these conditions, however, today, the climatic changes we are facing subject the crops to unforeseen threats, such as unseasonable rainfall, hail or frosts that are much more severe than usual, or above-normal levels of solar radiation that change the environmental conditions needed to successfully grow
certain fruits or vegetables.

Certain fruits, such as grapevines, are very sensitive to the presence of permanent moisture, especially the moisture created by rainfall in a non-warm period, which leaves moisture among the grapes and clusters that does not evaporate; this situation, in addition to the normal dust or dirt that is found on the fruit, produces ideal conditions for the resulting growth of fungi, mold and pests.

Also, as a result of climate change, as mentioned above, the fruit is subjected to high solar radiation exceeding the desired levels of sun, which can even end up damaging the fruit, modifying maturation and coloration patterns or undesirably increasing the sugar levels produced in the fruit.

There have been a number of solutions that have tried to solve these problems, which can be found in the prior art, however none of them have achieved optimization in its broadest sense, because even if they could solve the problem of protecting the fruit, they are costly solutions both in regards to production as well as their complex installation.

For example, one of solutions that has been considered is based on the placement of bags around the fruit, specifically the grape clusters, where the bags, usually made of plastic, have pores or openings for the release of vapors and incorporate areas of material that scatter light, so that they can protect against rain and sun; nevertheless, these solutions have proven to be ineffective, in particular because the bags fully cover the grape clusters and, despite having pores for the release of vapors, there is still the presence of fungi growing between the grapes, such is the case of the solutions shown in documents JPH1052180 by Hisaji Yuzo, published on 24 Feb. 1998 and CN101990835 by Daiki Yamada, published on 30 Mar. 2011; in both documents the disadvantage is not only the aforementioned, but that they are also complex devices to install due to their tubular shape that must be moved around the fruit, and, because they require a closure accessory, such as wire or tape to tie one end of the bag to the stem of the cluster, this means that the device has a minimum of two parts, adding to this the hours of work and diligence of the operator who installs the device and the possibility of losing the accessory or having it damage the stem.

There is also the document ES0193383 by Amelia Navarro, published on 28 Jul. 1975, which tries to provide a solution to the complexity issue for installing the protective bag, designed with an adjustment system that incorporates a metallic strap or wire along one of the bag's edges, in such a way that the strap is folded onto itself to close around the cluster, nevertheless, this solution lacks other necessary characteristics, seeing as the bag is tubular and encloses the cluster in a confined space that leaves no room for its unimpeded growth and does not facilitate the intervention of the operator during cultivation, since, in order to gain access to the cluster to monitor it or thin out some of the grapes, they would have to open the bag and move it in order to remove it and then place it back on; this latter disadvantage also applies to the two documents first mentioned.

Other solutions have been developed subsequently that try to avoid confining the fruit or clusters within bags with limited walls, with the appearance of umbrella-like devices that only partially cover the fruit, specifically in its upper area, leaving the entire lower area exposed to give it free space to grow and prevent the concentration of moisture within the bags.

These solutions are based on the presence of a sheet made of a semi-rigid material with a specific cut or groove that enables it to be folded or bent to achieve the shape of an umbrella placed on the fruit or cluster, in addition to an area made of the same material surrounding the stem, which can be seen in the contents of document CN201222908 by Basiti Wubulitalifu, published on 22 Apr. 2009; the main disadvantages of this device is that, on the one hand, it has a stem cover in a cylindrical form, which is difficult to adapt to all sizes and shapes of stems, seeing as by their nature, they come in all different lengths, widths and curvatures, meaning that this cover is limited in its application; on the other, it also has the disadvantage of how it is attached to the end of the sheet, since it has a layer of glue or adhesive material on the edges that touch each other, which means not only a higher cost and production complexity, but also that from a functional point of view, it is possible to lose this adhesiveness due to both poor handling by the operator as well as the moisture itself during use. These disadvantages could be accompanied by the materiality of the device, which if made of paper or something similar, could easily lose stiffness as a result of moisture, ending up folded down and sticking to the fruit.

There are solutions that have tried to overcome the above, such as that which in appears in documents CN201349435 by Jianjun Geng, published on 25 Nov. 2009 and JPH10165010 by Toida Masatoshi, published on 23 Jun. 1998, which are based on similar devices in that they involve sheets with a special cut to fold or bend around the fruit, however the proposals do not include a piece that covers the stem and the sheets are made of a semi-rigid plastic material or paper reinforced with a layer of fiber or resin, which allows for easy folding or bending of sheet, also delivering good water resistance, so that the shape would not change in wet conditions. The problem or disadvantage of these solutions is mainly the means of closing or attaching the edges of the cut or groove of the device, the case of CN201349435 describes a means of attaching the edges by applying adhesive tape, while JPH10165010 proposes using a bracket for closure.

In the case of CN201349435, the same thing happens as what was already mentioned with the application of adhesive, that is to say, it not only makes the production of the device more expensive by having to add a step and adhesive material, but also makes it difficult to install with the possibility of losing the adhesiveness due to the moisture itself. Another noteworthy disadvantage of this device is that it has a circular shape, which in terms of production generates a greater loss of excess material compared to what is achieved with a square or polygonal shape, as seen in JPH10165010, which shows a square shaped sheet, nevertheless, this last document that shows one of the better solutions known so far, has the disadvantages of lacking a good connection system, seeing as on the one hand, the groove can easily move forward and continue to crack the sheet and, on the other hand, it proposes the use of a bracket that joins the overlapping edges of the sheet to bend the device, and although it does not run the risk of peeling off like an adhesive, its application entails the use of an accessory device (stapler etc.) and the possibility of the operator wrongly placing the overlapping edges and brackets without making sure that both sides are smooth, with the possibility of one of the sheets ending up lifted or curved in the process of rapid stapling, creating a water inlet cavity, with the consequent accumulation of moisture and growth of fungi.

Of all the prior art solutions mentioned above, it is clear that none of them fully solve both the functional and production problems, since in some cases the devices are complex, with more than one piece, with additional accessories that complicate or add steps to their installation, with means of attachment that can peel off or be poorly attached creating water inlet cavities, leaving their effectiveness to depend on a careful installation by the operator; there are also other cases of devices with shapes that do not adapt to the shape of the fruit but instead confine it, as in the case of the bags.

Although some solutions offer a better alternative with a lower production cost, none of the existing solutions are able to solve the problem of excess ultraviolet radiation (UV) to which the fruit may be subjected, nor do they solve the problem of preventing the growth of fungi in the upper area of the fruit that remains in contact or near to the inner side of the protective sheet, nor do they offer the possibility of reuse, seeing how all solutions based on umbrella-shaped sheets have a means of attachment that are not reversible, meaning that once they have been attached the device must be broken in order to remove or dismantle it from the fruit or cluster of grapes, rendering it unusable.

According to the state of the solutions in the prior art that have been found until now, the invention included in this application aims to overcome all of the previously described problems, doing so in an integral manner that manages to solve the functional and production-related problems, and as such the purpose of the present invention is to provide a cover for fruit or clusters of fruit during the cultivation process that protects them from rain, preventing them from getting wet and inhibiting the growth of fungi, mold, etc.

A further purpose of the invention is to provide a cover for fruit or fruit clusters in the cultivation process that protects them from excess ultraviolet radiation.

Another further purpose of the invention is to provide a cover for fruit or clusters of fruit in the cultivation process with a simple shape, made from one piece, which results in a device with a low production cost.

Another further purpose of the invention is to provide a cover for fruit or clusters of fruit in the cultivation process with a low-complexity installation that does not require accessory elements for its assembly and ensures just one possible position of the parts, reducing the chances of error during installation.

Another further purpose of the invention is to provide a cover for fruit or clusters of fruit in the cultivation process that allows for its reuse.

DESCRIPTION OF THE INVENTION

This invention refers to a protective covering for developing hanging fruit, which protects the fruit from different environmental and climatic conditions, such as rain, frost, fungus growth, excess UV radiation and damage caused by birds, the cover being waterproof and a UV (ultraviolet) radiation blocker that is fitted individually on each fruit or cluster of fruit and is easy to install and reusable.

The protective cover is comprised mainly of an expanded polyethylene sheet (EPE) that has a main straight cut running from the midpoint of the flat geometric figure to one of the edges of the sheet and an arrangement of cuts and grooves that make up the connection system when the cover is fitted on the fruit.

The sheet that makes up the protective cover is made of an ultraviolet radiation blocking expanded polyethylene material (EPE-UV), comprised of a mixture of nucleating materials, foam, virgin resin and additives; in order to provide protective conditions against ultraviolet radiation, specifically the material is an expanded polyethylene foam, which includes a UV filter as an additive.

The material of the protective cover can include an additive that acts to prevent or attack the growth of fungi, mold or similar pests, by means of adding an antifungal agent to the material.

The sheet that makes up the protective cover made of EPE-UV material, has a thickness that can vary between 1 and 5 millimeters, and its weight varies between 26 and 84/m2.

The thickness of the sheet is in relation to the dimensions of the sides of the sheet, such that for a larger sized cover the thickness of the material is also greater, in order to not to lose the required stiffness of the material so that the cover can fulfill its function as an umbrella and so that it does not bend downwards falling or resting on the fruit, or result in a very thin sheet that is ultimately too fragile and breaks easily with simple handling during its installation.

Similarly, a very large thickness of a smaller sheet, in addition to costing more, can result in a sheet that is too rigid, difficult to handle and install.

It is important to mention that the weight of the material also affects the amount of light that reaches the fruit, as it is important that the cover is not completely opaque creating only shade, but that it also allows for the controlled passage of sunlight.

The shape of the sheet is a flat geometrical figure, which can be a polygonal shape selected from a square, rectangle or rhombus, in addition to being circle-shaped or elliptical.

In the case of the geometrical figure being a polygonal, the edges of its sides can measure between 200 and 300 millimeters, whereas if it is a circle these dimensions are associated with the length of the diameter.

The main straight cut running from the midpoint of the geometric figure to one of the sides of the sheet, can go to the midpoint of either side of the geometric figure or can go from the midpoint of the figure to any of the vertices of the figure. This main straight cut is what enables the areas of the sheet, adjacent to the cut, to overlap each other, causing the deformation of the sheet in such a way that it goes from being flat to having a cone-shaped laminar body placed over the fruit or cluster of grapes it protects.

A small perforation is located in the center of the sheet, where the indicated main straight cut originates, this being the area of the sheet that surrounds the stem of the fruit when the cover is fitted.

This central perforation fulfils two essential functions, one of which is to facilitate the arrangement of the sheet around the stem, and the other is to prevent the main straight cut from moving beyond the center from where it originates, a fact that, if it were to happen, could break the sheet, it would create a very large opening in the sheet to fit around the stem and therefore would form an entry point for water leading to the fruit right in the attachment area of the stem, preventing the cover from fulfilling its protective function for which it was designed.

The sheet's central perforation, which surrounds the fruit stem when the cover is on the fruit, can be circular, it can have the shape of a smaller straight cut perpendicular to the main straight cut or it can have the shape of a four-pointed star (crow's feet), where the shape of these perforations attempts not only to prevent the sheet from cracking, but also to fit as closely around the stem of the fruit as possible, like a seal, to prevent the passage of raindrops or moisture into the interior or inner surface of the protective cover.

For the perforations in the shape of a four-pointed star or a perpendicular straight cut, when installed around the stem, what happens is that the ends of the material are folded upwardly around the stem, creating a seal; a fact that is further facilitated by the characteristics of the material, as it has certain elasticity that allows for a slight stretch to fit around the stem, and as such the size of the perforations should not exceed 10 millimeters, both for the circular perforations and the other two, since although it may seem big, once it is wrapped around the stem, one part of the sheet overlapping over the other, the size of the central perforation reduces, the diameter and shape of the fruit stem being adequately adjusted.

The connection system for the cover consists of a set of cuts and grooves that create areas in the shape of arrowheads, and attachment incisions that are comprised of straight cuts where these arrowheads are inserted, managing to join the overlapping areas of the sheet.

The arrowhead areas can be shaped by two straight cuts of equal length, aligned on the same line and separated from each other by a distance determined by the length of the attachment incisions where they are inserted, this distance being equal to or less than the length of said attachment incisions.

These straight cuts that make up the arrowhead are positioned such that the outer end of one of the cuts is bordered by one edge of the sheet and the other outer end of the cut is bordered by the main straight cut, oriented at a 45° angle relative to said edge and main straight cut.

Alternatively, the straight cuts that make up the arrowhead can be located such that the outer end of one of the cuts is bordered by an edge of the sheet, and the edge of the outer end of the other cut borders the perpendicular edge, oriented at 45° relative to both edges.

Another option for making up the areas in the shape of an arrowhead is with two straight cuts of equal length between them, aligned and separated by a distance determined by the length of the attachment incisions where it is inserted, the cuts in turn are placed parallel and near to one of the edges of the sheet, from whose outer ends of both cuts originate diagonal cuts converging at 45° that border the parallel edge, creating a trapezoid shape.

In a basic configuration of the sheet there can only be one arrowhead and only one incision for inserting said arrowhead, while other possible configurations offer more than one set of cuts and grooves; this is in order for the ends of the two areas of the sheet that overlap each other to be inserted together, thus preventing one of the ends from releasing itself and twisting or bending, while also facilitating installation by the operator, seeing as the operator does not need to think about which side of the sheet goes over the other, instead any sheet that is placed on top of another will have a point of attachment, without there being a free end.

In the first described case, where the sheet only has one attachment incision and one arrowhead area, said attachment incision is located to one side of the main straight cut of the sheet, and the cuts making up the attachment incisions are located on the other side of the main straight cut, so that they match up upon insertion when the cover is fitted on the fruit.

In the other cases, where the cover has more than one attachment assembly, it may occur that there are two attachment incisions located on one side of the main straight cut, whereas on the opposite side there are two arrowheads; in another option there could be an attachment incision and an arrowhead to one side of the main straight cut, whereas on the the opposite side there is another attachment incision and arrowhead, such that they match up upon insertion when the cover is fitted on the fruit.

DESCRIPTION OF THE FIGURES

It should be pointed out that the accompanying figures of drawings only act as support elements to better understand the invention, without representing a protective covering for hanging developing fruit on a real and/or proportional scale, nor do they include details for the protective cover in its real operating condition. The invention can also not be limited to just that which appears in the figures, since they represent the most significant elements of the invention and may not include elements which are of general knowledge in the prior art. Therefore.

DETAILED DESCRIPTION OF THE INVENTION

This invention relates to a protective cover (1) for developing hanging fruit, which protects the fruit from different environmental and climatic conditions, such as rain, frost, fungus growth, excess UV radiation and damage caused by birds, the cover being waterproof and a UV (ultraviolet) blocker that is fitted individually on each fruit or cluster of fruit and is easy to install and reusable.

Figure 1:
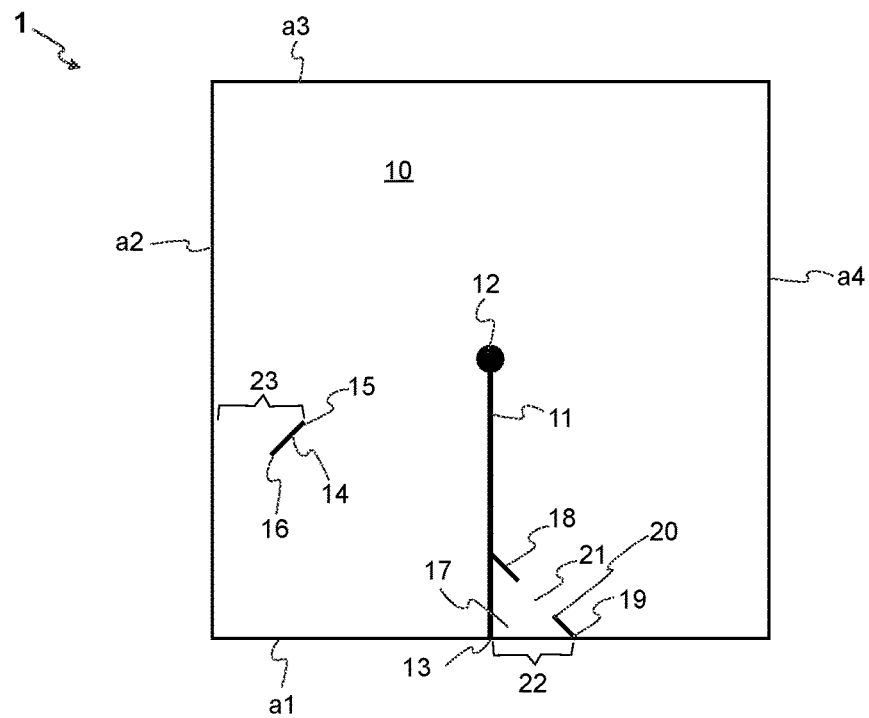
FIG. 1 shows a front view of the sheet, in template form, of the protective cover's first configuration alternative, with a circular central perforation, a single arrowhead and a single complementary attachment incision.

The protective cover (1), as seen in FIG. 1, is made up of an expanded polyethylene sheet (10) that has a main straight cut (11) running from a central perforation (12) of the geometric figure to one of the edges of the sheet, and an arrangement of cuts and grooves which make up the attachment system when the cover is fitted on the fruit.

The sheet (10) that makes up the protective cover is made of an ultraviolet radiation blocking expanded polyethylene material (EPE-UV), comprised of a mixture of nucleating materials, foam, virgin resin and additives; for the specific purpose of providing protective conditions against ultraviolet radiation, the material is made from polyethylene foam, which includes
a UV filter as an additive.

Said materials that make up the composition, can be selected, among others, from the following list:

Nucleate: PE Masterbatch MBT 3372 Marzullo or PE 100165-SA AMPACET.

Foam: Foam GMS PE Masterbatch or Foam GMS AE-ESP 9686 Marzullo.

Virgin resin: PEBD FILM EQUISTAR NA 235-013, PEBD FILM REPSOL 2221 FG,

PEBD HANWHA 5320, PEBD FILM EQUISTAR NA 345-196, PEBD FILM BRASKEM

EF 2222 or PEBD FILM PEMEX PX 20020 X.

UV Filter: CESA® LIGHT UV PE-531915.

The material of the protective cover (1) can include an additive that acts to prevent or attack the growth of fungi, mold or similar pests, by adding an antifungal agent.

The sheet (10) that makes up the protective cover (1) and is made of EPEUV material, has a thickness that can vary between 1 and 5 millimeters, and its weight varies between 26 and 84 g/m2.

The shape of the sheet (10) is a flat geometrical figure, which can be a polygonal shape selected from a square, rectangle or rhombus, in addition to being circle-shaped or elliptical.

In the case of the geometrical figure being a polygonal, the edges of its sides can measure between 200 and 300 millimeters, whereas if it is a circle these dimensions are associated with the length of the diameter.

As demonstrated by FIG. 1, the sheet (10) is square with equal sides (a1, a2, a3, a4), where the main straight cut (11) runs from the circular central perforation (12) of the geometric figure to the midpoint (13) of the side (a1) of the geometric figure; while the means of attachment are made up of an attachment incision (14) located on one side of the main straight cut (11), which has an upper end (15) and a lower end (16), and is oriented at an angle to the main straight cut (11), while on the opposite side of the main straight cut (11) there is a tab in the shape of an arrowhead (17), which is made up of two straight cuts (18) aligned with each other, each with an outer end (19) and an inner end (20), wherein said cuts are linearly spaced from each other creating a separation gap (21) between them and wherein said straight cuts (18) are diagonally oriented, touching, on one side, the main straight cut (11) and, on the other, the side (a1) of the sheet (10).

The length of the separation gap (21) of the arrowhead-shaped tab (17) is equal or less along the length of the attachment incision (14), while the distance (22) given between the main straight cut (11) and the outer end (19) of the straight cut (18) which touches the side (a1) of the sheet, has a length equal to the distance (23) which is given, in a straight line, from the upper end (15) of the attachment incision (14) to the edge of the side (a2) of the sheet (10).

In the protective cover's (1) assembly position, the sheet (10) is placed above the fruit, wrapping around the stem with the edge of the circular central perforation (12), while the area to the right of the main straight cut (11) passes over the left-hand area, one side overlapping the other, while the arrowhead-shaped tab (17) is inserted into the attachment incision (14) until the separation gap (21) fits into said attachment incision (14).

Figure 2:
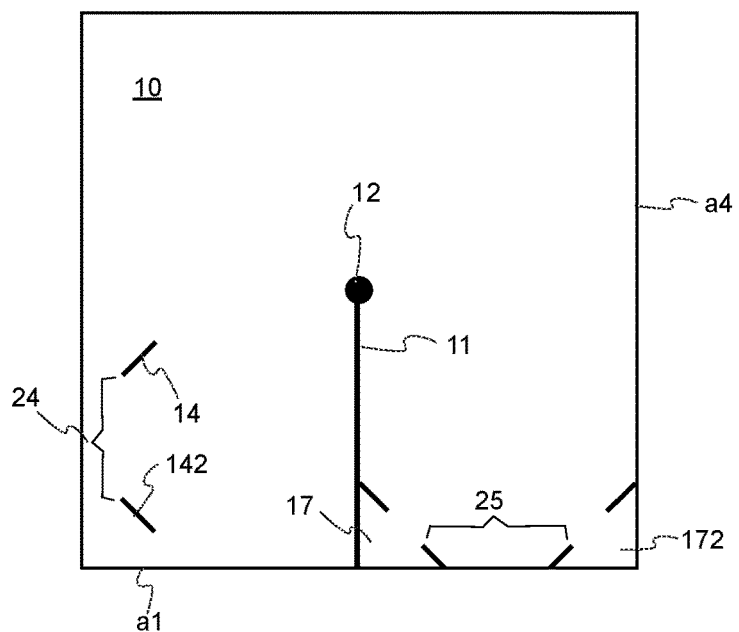
FIG. 2 shows a front view of the sheet, in template form, of the protective cover's second configuration alternative, with a circular central perforation, with two arrowheads and two complementary attachment incisions.

FIG. 2 shows a second configuration alternative, wherein the sheet (10) has the same basic elements as the alternative in FIG. 1, however it has an additional second attachment incision (142) that is the same as the first but oriented at an opposite angle and located lower down on the same vertical line; while the side opposite the main straight cut (11) has a second arrowhead-shaped tab (172), same as the first, but oriented at an opposite angle and located at the apex where sides (a1) and a (4) of the sheet are.

In this case, the vertical distance (24) between the two attachment incisions (14) and (142) is equal to the horizontal distance (25) between the separation gaps of each tab (17) and (172). In its assembly position, the sheet (10) is placed above the fruit, wrapping around the edge of the circular central perforation (12), while the area to the right of the main straight cut (11) passes above the left-hand area, one side overlapping the other, while the arrowhead-shaped tab (17) is inserted into the attachment incision (14) and simultaneously the second arrowhead-shaped tab (172) is inserted into the second attachment incision (142).

Figure 3:
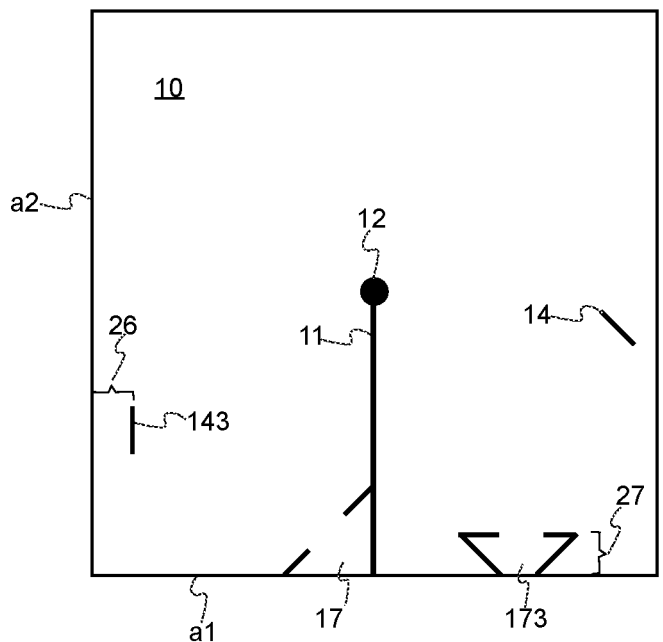
FIG. 3 shows a front view of the sheet, in template form, of the protective cover's third configuration alternative, with a circular central perforation, a single arrowhead and attachment incision to one side of the main cut, and an attachment incision with a trapezoidal arrowhead on the other side of the main straight cut.

FIG. 3 shows a third configuration alternative, wherein the sheet (10) has the same basic elements as the alternative in FIG. 1, however in this case on one side of the main straight cut there is a slanted upper attachment incision (14) and on the same side, but bordering the lower side (a1) of the sheet (10), there is a type of trapezoidal tab (173) located in the middle of that side; while on the opposite side of the main straight cut (11) there is a vertical attachment incision (143) and an arrowhead-shaped tab (17) located on the lower right apex of that side of the sheet. The vertical attachment incision (143) is located at the halfway point of said main straight cut (11) but at a distance (26) from the left side (a2)

of the sheet, wherein said distance (26) is equal to the distance (27) between the trapezoidal tab (173) and the lower side (a1) of the sheet.

In this case, in its assembly position, the sheet (10) is placed above the fruit, wrapping around the edge of the circular central perforation (12), while the area to the right of the main straight cut (11) passes above the left-hand area, one side overlapping the other, while the arrowhead-shaped tab (17) is inserted into the slanted attachment incision (14) and simultaneously the trapezoidal tab (173) is inserted into the vertical attachment incision (143).

Figure 4:
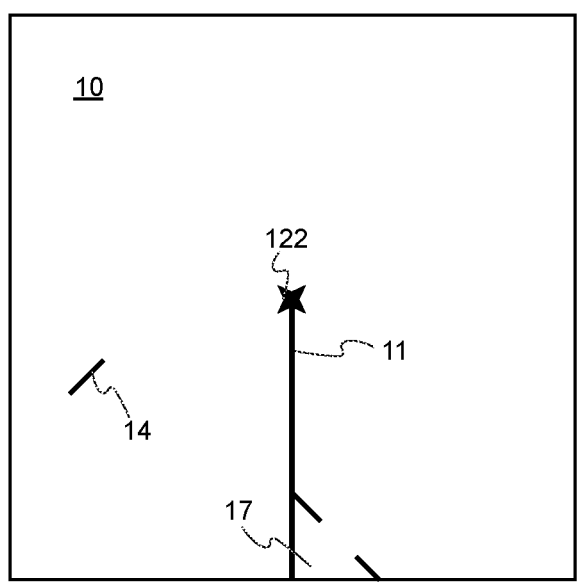
FIG. 4 shows a front view of the sheet, in template form, of the protective cover's fourth configuration alternative, with a central perforation in the shape of a four-pointed star, an arrowhead and attachment incision to one side of the main straight cut and an attachment incision with a trapezoidal arrowhead on the other side of the main straight cut.
Figure 5:
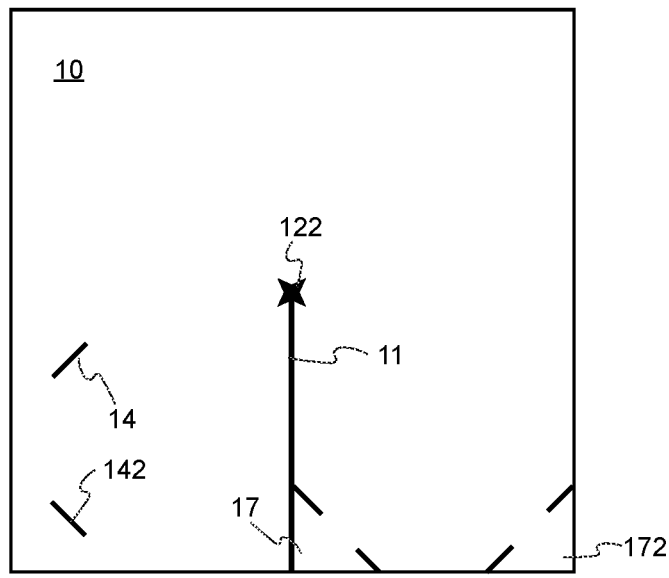
FIG. 5 shows a front view of the sheet, in template form, of the protective cover's fifth configuration alternative, with a central perforation in the shape of a four-pointed star, with two arrowheads and two complementary attachment incisions.
Figure 6:
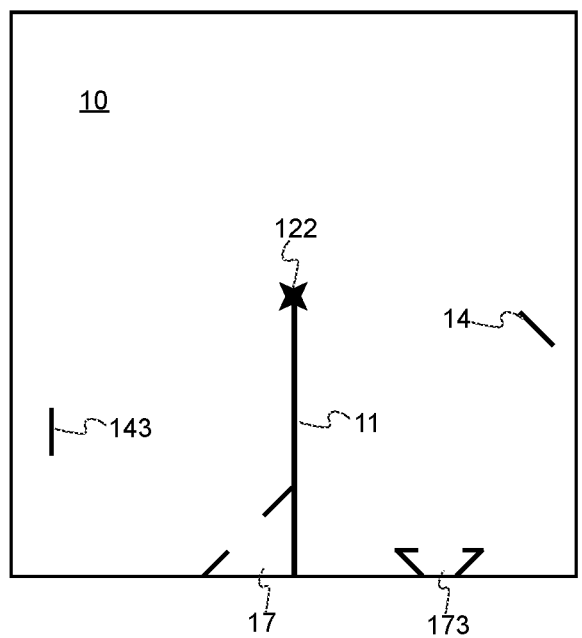
FIG. 6 shows a front view of the sheet, in template form, of the protective cover's sixth configuration alternative, with a central perforation in the shape of a four-pointed star, with an arrowhead and attachment incision to one side of the main straight cut and an attachment incision with a trapezoidal arrowhead on the other side of the main straight cut.

FIG. 4, FIG. 5 and FIG. 6 respectively show a fourth, fifth and sixth alternative configuration of the sheet (10), where the alternative in FIG. 4 shows a configuration that is the same as the first alternative, i.e. a main central cut (11), a tab (17) and an attachment incision (14), located in the same place, however they differ in that the central perforation has the shape of a four-pointed star (122).

The alternative in FIG. 5 shows a configuration that is the same as the second alternative, i.e., a main central cut (11), tabs (17), (172) and attachment incisions (14), (142), located in the same place, however they differ in that the central perforation has the shape of a four-pointed star (122).

The alternative in FIG. 6 shows a configuration that is the same as the third alternative, i.e., a main central cut (11), tabs (17), (173) and attachment incisions (14), (143), located in the same place, however they differ in that the central perforation has the shape of a four-pointed star (122).

Figure 7:
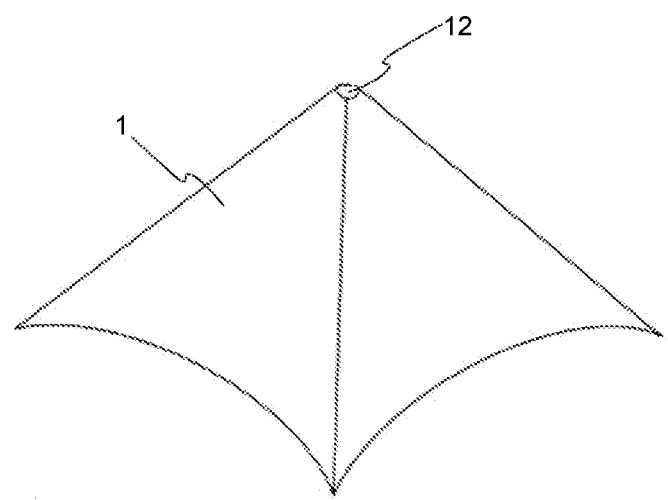
FIG. 7 shows an exemplary perspective view of the protective cover when fitted.

FIG. 7 shows an approximate perspective view of the protective cover when it is being assembled, that is, when the arrowhead-shaped tab has already been fit into the attachment incision (not shown in the figure), so that the protective cover is set up in its "umbrella" shape.

Figure 8:
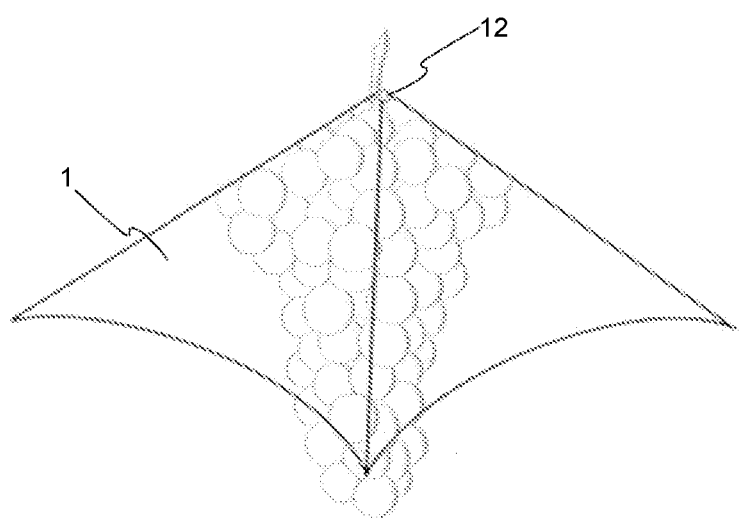
FIG. 8 shows an exemplary perspective view of the protective cover fitted around the stem and on a cluster of grapes.

FIG. 8 shows an approximate perspective view of the protective cover fitted around the stem and on a cluster of grapes. As can be seen, the cluster of grapes is under the protective cover, which is attached to the stem by means of the central perforation (12). Note that initially the protective cover has the shape of a flat sheet with the respective incorporated cuts, and at the time of use, the fruit stem passes through the main straight cut (11) until reaching the central perforation (12), then the arrowhead-shaped tab is fit into the attachment incision (not shown in the figure), so that the protective cover can be fitted in its "umbrella" shape over the fruit.

It is worth noting that the protective cover of the present invention can be fitted on any type of fruit that grows hanging from the tree or plant from which it originates, not only being limited to clusters of grapes, other fruits on which the protective cover can be fitted include, for example: apples, peaches, lemons, oranges, kiwis, grapefruits, pears, etc.

What is claimed is:

1. A waterproof and UV (ultraviolet) radiation blocking protective cover (1), for hanging developing fruit, comprising: a sheet (10) made of an expanded polyethylene material, the expanded polyethylene material is an ultraviolet radiation blocking (EPE-UV) material having a flat geometric shape, with a main straight cut (11) from a central perforation (12) to a midpoint (13) of an edge of the sheets and an attachment system comprised of an arrangement of cuts; wherein the EPE-UV material consists of a mixture of nucleating materials, foam, virgin resin and an additive selected from the group consisting of: a UV filter and an antifungal agent.

2. The waterproof and UV radiation blocking protective cover (1), in accordance with claim 1, wherein the central perforation (12) is a circular perforation (12) in the center of the sheet (10), where the main straight cut (11) originates, which surrounds a stem of the fruit when the cover is fitted on the fruit.

3. The waterproof and UV radiation blocking protective cover (1), in accordance with claim 1, wherein the central perforation (12) is a four-pointed star-shaped perforation (122) in the center of the sheet (10), where the main straight cut (11) originates, which surrounds a stem of the fruit when the cover is fitted on the fruit.

4. The waterproof and UV radiation blocking protective cover (1), in accordance with claim 1, wherein the EPE-UV material is an expanded polyethylene foam, which includes a UV filter as the additive.

5. The waterproof and UV radiation blocking protective cover (1), in accordance with claim 1, wherein the EPE-UV material is an expanded polyethylene foam ich includes a UV filter as the additive.

6. The waterproof and UV radiation blocking protective cover (1), in accordance with claim 1, wherein the EPE-UV material has a thickness between 1 and 4 millimeters, and a weight between 26 and 84 g/m2.

7. The waterproof and UV radiation blocking protective cover (1), in accordance with claim 1, wherein the shape of the sheet (10 is selected from: a square, rectangle, rhombus or circle.

8. The waterproof and UV radiation blocking protective cover (1), in accordance with claim 7, wherein the shape of the sheet (10) is a square or circle.

9. The waterproof and UV radiation blocking protective cover (1), in accordance with claim 8, wherein the shape of the sheet (10) is a square, the square shape of the sheet (10) has sides whose edges measure between 200 and 300 millimeters.

10. The waterproof and UV radiation blocking protective cover (1), in accordance with claim 1, wherein the arrangement of cuts that make up the attachment system includes tabs in the shape of arrowheads (17, 172, 173) and attachment incisions (14, 142, 143) for the attachment of said arrowhead-shaped tabs.

11. The waterproof and UV radiation blocking protective cover (1), in accordance with claim 10, wherein at least one arrowhead-shaped tab of the arrowhead-shaped tabs (17, 172, 173) is located on one side of the main straight cut (11) of the sheet, and at least one attachment incision of the attachment incisions (14, 142, 143) is located on an opposite side of the main straight cut (11) in such a way that the at least one tab and the at least one attachment incision match up upon attachment when the cover (1) is fitted on the fruit.

12. The waterproof and UV radiation blocking protective cover (1), in accordance with claim 10, wherein at least one arrowhead-shaped tab of the arrowhead-shaped tabs (17, 172, 173) and at least one attachment incision of the attachment incisions (14, 142, 143), are located together on both sides of the main straight cut (11) of the sheet (10) in such a way that the at least one tab and the at least one attachment incision match up upon attachment when the cover (1) is fitted on the fruit.

13. The waterproof and UV radiation blocking protective cover (1), in accordance with claim 1, wherein the arrangement of cuts of the attachment system comprises two diagonally aligned cuts (18) forming an arrowhead-shaped tab (17) at the lower end en of one side of the main straight cut (11), and a cut forming an attachment incision (14) on another side of the main straight cut (11) opposite the one side.

* * * * *